United States Patent [19]

Rosenberg et al.

[11] Patent Number: 5,780,290
[45] Date of Patent: Jul. 14, 1998

[54] NON-POLLUTING COMPOSITIONS TO DEGRADE HYDROCARBONS AND MICROORGANISMS FOR USE THEREOF

[75] Inventors: Eugene Rosenberg; Eliora Z. Ron, both of Tel-Aviv, Israel

[73] Assignee: Ramot, University of Authority for Applied Research and Industrial Development, Israel

[21] Appl. No.: 461,754

[22] Filed: Jun. 5, 1995

Related U.S. Application Data

[63] Continuation of Ser. No. 994,493, Dec. 21, 1992, abandoned.

[30] Foreign Application Priority Data

Dec. 24, 1991 [IL] Israel ......................... 100485
Nov. 23, 1992 [IL] Israel ......................... 103842

[51] Int. Cl.⁶ ........................ C12N 1/00; C12N 1/38
[52] U.S. Cl. .................. 435/243; 435/244; 435/252.1; 435/262.5; 435/281; 435/821; 435/826; 435/834; 210/601; 210/922; 252/174.12
[58] Field of Search ................. 435/243, 244, 435/252.1, 262.5, 821, 834, 826, 281; 252/174.12; 210/922, 601

[56] References Cited

U.S. PATENT DOCUMENTS

| | | |
|---|---|---|
| 3,791,974 | 2/1974 | Borchert . |
| 3,959,127 | 5/1976 | Bartha et al. ............... 210/11 |
| 4,033,745 | 7/1977 | Moore . |
| 4,332,610 | 6/1982 | Sartoretto et al. . |
| 4,385,121 | 5/1983 | Knowlton . |
| 4,401,762 | 8/1983 | Tellier et al. ............... 435/243 |
| 4,460,692 | 7/1984 | Tellier et al. ............... 435/243 |
| 4,508,824 | 4/1985 | Olsen . |
| 4,521,515 | 6/1985 | Hata . |
| 4,850,745 | 7/1989 | Hater et al. . |
| 4,910,143 | 3/1990 | Vandenbergh . |
| 4,925,343 | 5/1990 | Raible et al. . |
| 4,992,174 | 2/1991 | Caplan et al. ............... 210/610 |
| 5,080,782 | 1/1992 | Caplan et al. ............... 210/151 |

FOREIGN PATENT DOCUMENTS

| | | |
|---|---|---|
| 1601882 | 9/1970 | France . |
| 2163877 | 7/1973 | France . |
| 2654909 | 6/1977 | Germany . |

OTHER PUBLICATIONS

National Environmental Technology Applications Center Summary Report, Tier II Bioremediation Agent Evaluation Testing of System E.T. 20 Formulation With Marine Aquarium Water, University of Pittsburg Applied Research Center 615 William Pitt Way, Pittsburg, PA 15238 (Apr. 1995).

Atlas, Ronald M. "Bioremdiation", C&EN, Apr. 3, 1995, pp. 1–2, 32–42.

Rosenberg, Eugene et al. "Petroleum Bioremediation—A Multiphase Problem", Biodegredation 3:337–350, 1992, pp. 213–350.

National Environmental Technology Applications Center Summary Report, Bioremediation Agent Evaluation, System T. 20 Formulation, University of Pittsburg Applied Research Center, 615 William Pitt Way, Pittsburg, PA 15238 (Apr. 1993).

Gutnick et al. "Oil Tankers and Pollution: A Microbiological Approach", Ann. Rev. Microbiol. 1977, 31:379–96.

Vanosa et al. "Protocaol for Testing Bioremediation Products Against Weathered Alaskan Crude Oil," Oil Spill Conference, San Diego, CA, 4–7, Mar. 1991, pp. 563–570.

Atlas et al, "Stimulated Biodegradation of Oil Slicks Using Oleophilic Fertilizers," Environmental Science and Technology (1973) vol. 7, No. 6, p. 538.

(List continued on next page.)

*Primary Examiner*—Helen Pratt
*Attorney, Agent, or Firm*—Cushman Darby & Cushman IP Group of Pillsbury Madison & Sutro

[57] ABSTRACT

The present invention relates to compositions containing bacteria capable of degrading hydrocarbons, such as petroleum or petroleum products and methods for their use.

3 Claims, 2 Drawing Sheets

OTHER PUBLICATIONS

Laudels et al, "Controlled Release Fertilizers,", Chemical Economic Handbook, SRI International (1990).

Chianelli et al., "Bioremediation Technology Development and Application to the Alaskan Spill," 1991 Oil Spill Conference, San Diego, CA, 4–7, Mar. 1991, pp. 549–558.

Glaser, et al, "Development and Evaluation of Application Techniques for Delivery of Nutrients to Contaminated Shoreline in Prince William Sound," 1991 Oil Spill Conference, San Diego, CA, 4–7, Mar. 1991, p. 559.

Safferman S., "Selection of Nutrients to Enhance Bioremediation for the Remediation of Oil Spilled on Beaches" 1991 Oil Spill Conference, San Diego, CA, 4–7, Mar. 1991, p. 571.

NON-POLLUTING COMPOSITIONS TO DEGRADE HYDROCARBONS AND MICROORGANISMS FOR USE THEREOF

This is a continuation of application Ser. No. 07/994,493, now abandoned, filed on Dec. 21, 1992.

BACKGROUND OF THE INVENTION

The present invention relates to compositions containing bacteria capable of degrading hydrocarbons, such as petroleum or petroleum products, and complex nitrogen-containing materials such as urea-formaldehyde resins and other compatible polymers as the source of nitrogen, a method enhancing the biodegradation of hydrocarbons and biologically pure cultures of bacteria.

Bacterial degradation of petroleum hydrocarbons has been known and recognized for decades. The subject has been reviewed comprehensively in the literature, examples being CRC Critical Reviews in Biotechnology, Volume 3, Issue 3, "Microbial Surfactants" by E. Rosenberg and "Report on the 1991 Oil Spill Conference", San Diego, Calif., 4–7 Mar. 1991 and references cited therein, whose contents are incorporated by their mention.

Reports have been published that show the bioremediation of hydrocarbons in closed vessels (as described in U.S. Pat. No. 3,941,692) is effective, using almost any source of water-soluble inorganic nitrogen and phosphorous. However, studies have shown that bioremediation of oil on the open seas or on oil-polluted beaches was still a major problem. Initial growth is stopped or slowed down by the natural tendency of most nutrients and fertilizers to diffuse into the water or the adjacent ground and are, thus, under-used by the microorganisms. Said water-soluble nutrient and fertilizers also suffer from the fact that they enable the uncontrolled growth of numerous naturally-occurring microorganisms in the soil and water which then, themselves, become a serious cause of water pollution.

Various methods have been employed up to the present as described in U.S. Pat. No. 4,401,162, U.S. Pat. No. 4,460,692 and the references cited in the above described report from 1991. While some successes were obtained in the prior reports, the processes of biodegradation occurred very slowly over a period of months.

SUMMARY OF THE INVENTION

In accordance with the present invention, there are provided novel bacteria which are effective as bioremediation agents for petroleum pollution. There is also provided a composition of at least one microorganism capable of degrading hydrocarbons and utilizing complex insoluble organic nitrogen sources, as a source of nitrogen and optionally phosphorous wherein the organic nitrogen molecule of the complex nitrogen-containing material is not utilizable by most soil and water microorganisms in a mixture with a suitable carrier. There is further provided a method of enhancing the biodegradation and/or bio-emulsification of petroleum, which comprises contacting the petroleum with said composition so that the microorganism utilizes the petroleum as a source of carbon, thereby degrading the petroleum, without any substantial growth of the indigeneous competing microorganisms.

In a specific embodiment of the present invention the said composition contains at least one of the novel bacteria effective as a bioremediation agent for petroleum; and uses a urea-formaldehyde resin or other compatible polymers as a source of nitrogen.

Sea water (20 ml) containing 0.5% crude oil and 20 mg fertilizer UF-1 were inoculated with 20 µl of the mixed culture (three days growing) and incubated with shaking at 25° C. Samples were removed at various times for the determination of viable count (·) and turbidity (□).

Figure 2:
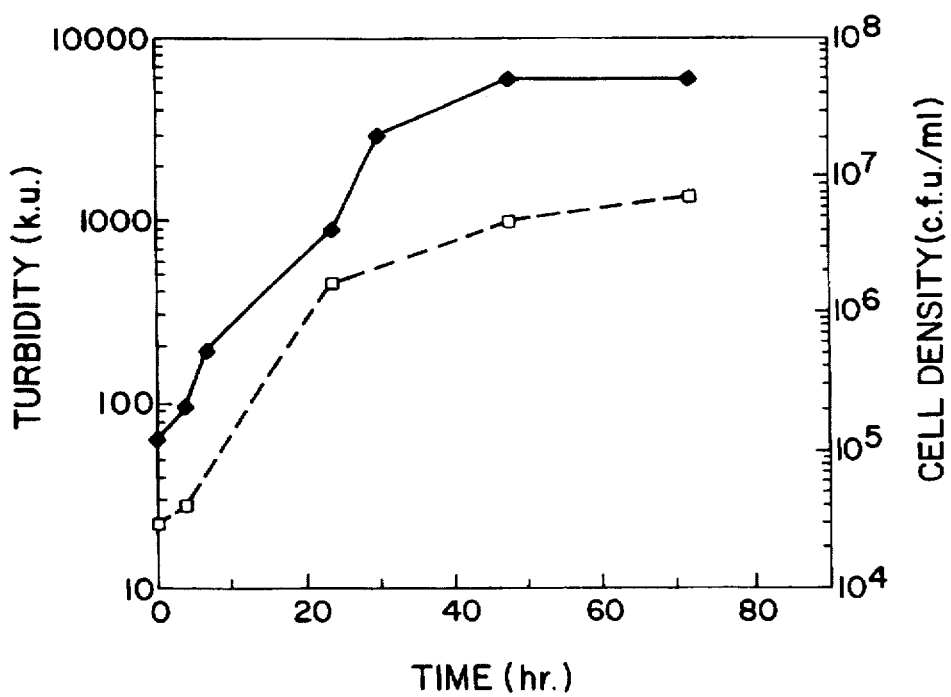

FIG. 2. Kinetics of Growth and Emulsification—Strain ER-RL3

Sea water (20 ml) containing 0.5% crude oil and 20 mg fertilizer UF-1 were inoculated with 20 µl of strain ER-RL3 (three days growing). The culture was incubated at 25° C. with shaking and at various times samples were removed for the determination of viable count (·) and turbidity (□).

Figure 3:
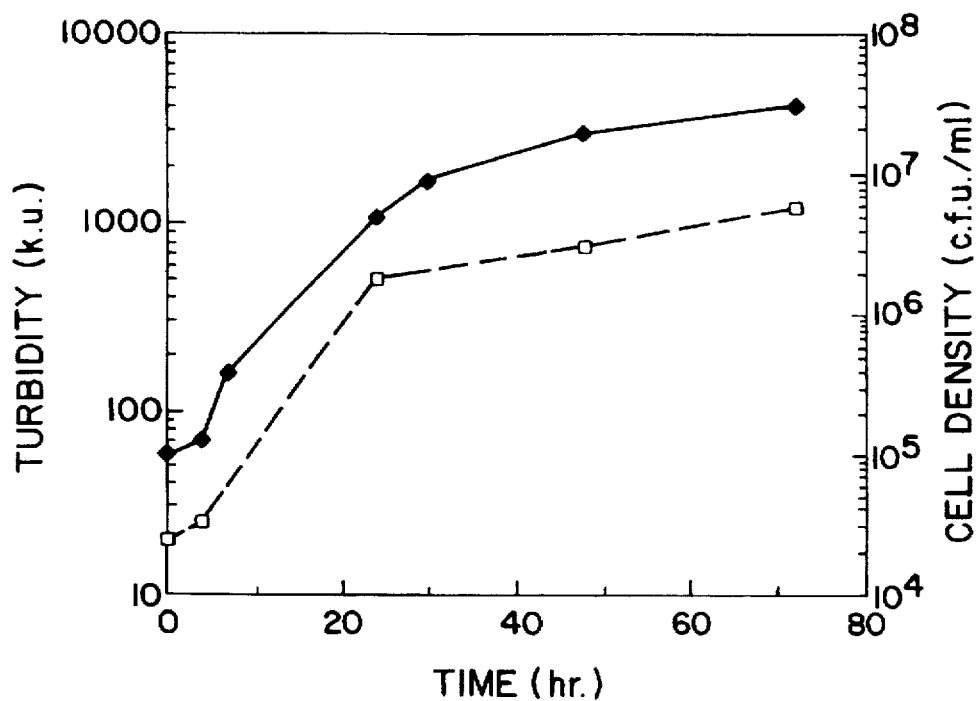

FIG. 3. Kinetics of Growth and Emulsification—Strain ER-RL4

Sea water (20 ml) containing 0.5% crude oil and 20 mg fertilizer UF-1 were inoculated with 20 µl of strain ER-RL4 (three days growing). The culture was incubated at 25° C. with shaking and at various times samples were removed for determination of viable count (·) and turbidity (□).

Figure 4:
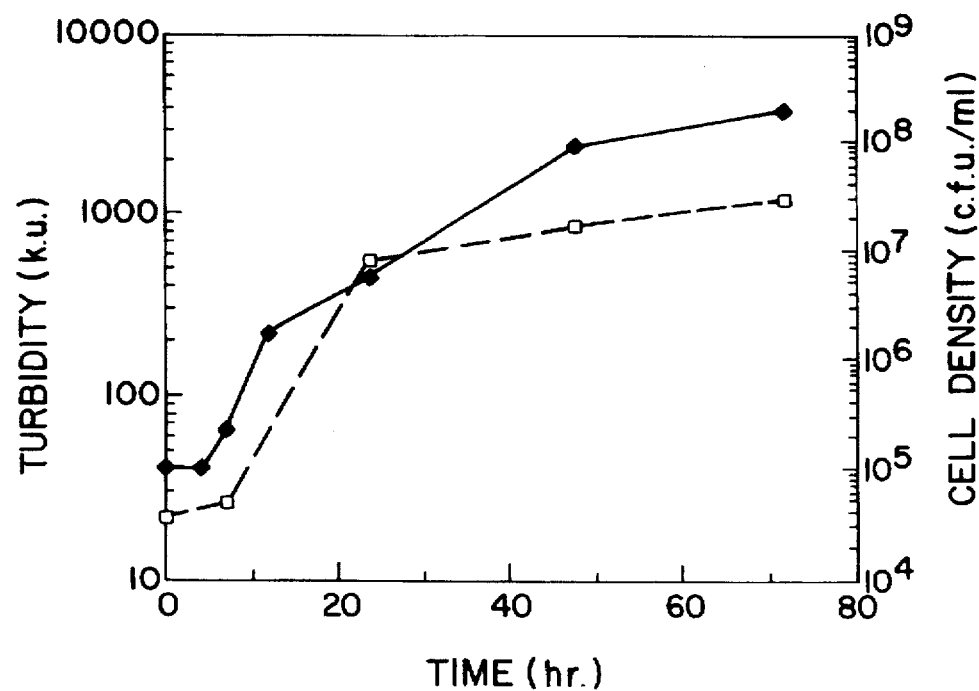

FIG. 4. Kinetics of Growth and Emulsification—Strain ER-RT

Sea water (20 ml) containing 0.5% crude oil and 20 mg fertilizer UF-1 were inoculated with 20 µl of strain ER-RT (three days growing). The culture was incubated at 25° C. with shaking and at various times samples were removed for determination of viable count (·) and turbidity (□).

DETAILED DESCRIPTION OF THE INVENTION

The novel bacteria were obtained by an enrichment culture procedure using crude oil as the carbon and energy source and a urea-formaldehyde resin, such as UF-1, as the source of nitrogen and phosphorous and sea water or tap water as the source of other minerals. In the case of sea water this afforded a mixed culture. Three different colony types were isolated by restreaking. These strains are referred to as ER-RL3, identified as *Pseudomonas alicaligenes* or *Alicaligenes*, ER-RL4, identified as *Pseudomonadaceas* genus Pseudomonas and ER-RT, identified as *Pseudomonadaceae* genus *Gluconobacter*. These strains were deposited with the National Collections of Industrial and Marine Bacteria Ltd. (NCIMB), Aberdeen, Scotland, pursuant to the provisions of the Budapest treaty on the International Recognition of the Deposit of Microorganisms for the Purpose of Patent Procedure on 16 Dec. 1991, under Accession Numbers NCIMB-40464, NCIMB-40465 and NCIMB-40466 for ER-RL3, ER-RL4 and ER-RT, respectively.

In the case of using tap water a mixed culture was also obtained. Two different colony types were isolated by restreaking. These strains are referred to as ER-RLD and ER-RLX, both identified as strains of *Acinetobacter calcoaceticus*. These strains were deposited with the National Collections of Industrial and Marine Bacteria Ltd. (NCIMB), Aberdeen, Scotland, pursuant to the provisions of the Budapest Treaty on the International Recognition of the Deposit of Microorganisms for the Purpose of Patent Procedure on 8 Jun. 1992, under Accession Numbers NCIMB-40506 and NCIMB-40507 for ER-RLD, ER-RLX respectively.

The urea-formaldehyde (UF) resins of the novel compositions of the present invention can be almost any type of UF fertilizer. Examples are described in *Controlled Release*

*Fertilizers* by Sarah P. Landels, A. Leder and N. Takei, Chemical Economic Handbook, SRI International, 1990, whose contents are incorporated by mention, and especially pages 535.800W–535.8001F.

UF Solutions

UF solutions contain no water-insoluble nitrogen but have nitrogen release periods estimated at eight to twelve weeks (compared with six to eight weeks for straight urea solutions), with nitrogen utilization by plants between 80% and 95%. These products are solutions of short-chain water-soluble UF compounds, principally methylol ureas and methylene diurea, and free urea. Most UF solutions contain from 26% to 30% nitrogen.

Methylol urea (MO) solution fertilizer products of Georgia-Pacific Corporation, Morral Chemical Company, and the Triazone Division of Arcadian Corporation contain 30% nitrogen. About half of the total nitrogen in these products is provided by UF compounds, principally methylol ureas, and about half is provided by unreacted urea. CoRoN Corporation markets an amine-modified polymethylene urea solution product that contains 28% nitrogen. Growth Products Division of C.P. Chemical Company, Inc. markets a methylene diurea (MDU) solution that analyzes 26% nitrogen. Methylene diurea polymers are the source of most of the total nitrogen in this product; less than 20% of the total nitrogen is supplied by free urea.

Companies marketing MO products emphasize the following claimed advantages over certain other soluble nitrogen sources (e.g., straight urea solutions): higher nitrogen content, lower water content, much higher "salt-out" temperature, much lower nitrogen phytotoxicity (i.e., burn potential), and moderate initial crop response (reducing the tendency of disease problems in some crops associated with a high initial response to urea applications).

Urea-Triazone Solution Fertilizers

N-SURE® (28-0-0), a new patented urea-formaldehyde-ammonia solution fertilizer product of the Triazone Division of Arcadian Corporation that was introduced in 1985, is unique because of the closed-ring configuration of its urea-formaldehyde-ammonia component, triazone. The triazone ring contains three nitrogen atoms that are bound by three carbon atoms, as shown in the structure diagram below.

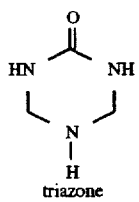
triazone

This structure is claimed to provide superior nonburning and storage characteristics as well as controlled release of nitrogen. As the triazone ring breaks down, the available nitrogen is released uniformly over an eight-to twelve-week period. N-SURE® is a liquid product designed for professional application to lawns and turf. A line of liquid fertilizer products based on urea-triazone (TRISERT®) also been designed for foliar application to high-value specialty agricultural crops. Additional applications of the new urea-triazone controlled release nitrogen technology are in experimental stages, as are other controlled release fertilizers and agricultural chemicals based on the triazone ring (i.e., analogs of triazone).

UF Suspensions (Suspension Methylene Ureas)

FLUF® 18-0-0, a patented product of W. A. Cleary corporation, is a microcrystalline dispersion of soluble and insoluble urea reaction products. It is made by reacting urea with UF concentrate and other higher aldehyde groups. Approximately 25% of the total nitrogen in this product is water-insoluble. FLUF® is toll manufactured for W. A. Cleary by Borden, Inc., Borden Chemical Division and by Morral Chemical Company. In addition to their toll production of FLUF® for W. A. Cleary, Morral Chemical manufactures a similar UF suspension product, UWIN, for Chem-Lawn Corporation and other professional lawn care and golf course accounts, and Borden Chemical manufactures its own patented UF suspension fertilizer, FER 700, for Chem-Lawn. RESI-GROW®, or GP-4318 is a similar liquid controlled release product that was introduced in 1984 by Georgia-Pacific Corporation.

Characteristics of the principal solid and liquid UF fertilizer products that are currently marketed in the United States are shown in the following table, which also identifies each product's manufacturer or primary supplier.

| | Urea-Formaldehyde Fertilizer Products Marketed in the United States - 1990 | | | |
|---|---|---|---|---|
| | | Water-Insoluble Nitrogen (WIN) | | |
| Product, Supplier, and Trade Name | Analysis (N-P-K) | Percent of Total N | Percent of Product Weight | General Use/Remarks |
| Solid Ureaform | | | | |
| NOR-AM Chemical Company* | | | | |
| Nitroform ® Blue Granular ™ | 38-0-0 | 71% | 27% | Uses include lawns and turf, trees and |
| Nitroform ® Blue Chips ® | 38-0-0 | 71% | 27% | shrubs, commercial nurseries and green- |
| Nitroform ® Powder Blue ® | 38-0-0 | 66% | 25% | houses, and specialty agricultural crops. Blue Granular ® was introduced in early 1988. Its larger particle size than Blue Chip ® makes it more suitable for blending with granular urea and other fertilizer materials. Manufacturing grade products, Gray Chip ® and Powder Gray ®, are the same as Blue Chip and Powder Blue ®, except in color. Nitroform ® is manufactured for NOR-AM by Hercules Inc. |
| O. M. Scott & Sons | | | | |
| Scotts Hi-Tech ® | 38-0-0 | 65% | 25% | A product developed for high-value vegetable crops. |
| Private label grades: Granuform ®HD | 38-0-0 | 71% | 27% | Granuform ® products are marketed to fertilizer blenders by |

Urea-Formaldehyde Fertilizer Products Marketed in the United States - 1990

| Product, Supplier, and Trade Name | Analysis (N-P-K) | Water-Insoluble Nitrogen (WIN) Percent of Total N | Percent of Product Weight | General Use/Remarks |
|---|---|---|---|---|
| Granuform ® Fine Grade | 38-0-0 | 65% | 25% | Wilson & Geo. Meyer & Co. A friable product suitable for ammoniation, compaction, or blending with other fine-grade materials. |
| Methylene Ureas | | | | |
| NOR-AM Chemical Company | | | | |
| Nutralene ™ | 40-0-0 | 32.5% | 13% | Since April 3, 1989, this product has been manufactured exclusively for NOR-AM by Homestead Research & Development Foundation, Slatersville, Rhode Island. Two grades are available, granular and chip. |
| O. M. Scott & Sons | | | | |
| Scotts ®Hi-Tech ® | 41-0-0 | 22% | 9% | A granular product for high-value vegetable crops that is marketed to fertilizer blenders by Wilson & Geo. Meyer & Co. |
| Scott ®Hi-Tech ® | 41-0-0 | 10.1% | 4% | A milled suspendable product for the professional lawn care market. |
| Scotts ® Proturf ®HD Nitrogen | 41-0-0 | 24.6% | 10.1% | Products for professional turf markets. |
| Scotts ® Proturf ®HD Nitrogen Plus | 30-0-0 | 19% | 5.7% | |
| Granulated Mixed Fertilizers Containing In Situ Methylene Ureas | | | | |
| Koos, Inc. | | | | |
| Green Turf ® | various | varies | varies | Nature's Best and Green Turf ® lines are produced for the consumer lawn and garden market. Turf-Terra Line is for golf courses. |
| Nature's Best ® | various | varies | varies | |
| Turf-Terra Premium | various | varies | varies | |
| Lebanon Chemical Corporation | | | | |
| Country Club ® | various | varies | 1.6%–10% | Country Club line of products is produced for golf courses and other professional turf markets. |
| Greens Keeper ® Greenview ® | various | varies | varies | Lawn and turf fertilizers. |
| Private Label Products | | | | |
| O. M. Scott & Sons | | | | |
| Scotts ® Pro Turf ® | various | 28%–55% | varies | Scotts ® line of products are produced for the consumer lawn and garden market. ProTurf ® line is for golf courses, other professional turf, and professional lawn care. ProGrow ® line is for commercial nurseries. |
| ProGrow ® | | | | |
| UF Solutions | | | | |
| Arcadian Corporation Triazone Division | | | | |
| Formolene Plus ® | 30-0-1 | 0% | 0% | A methylol urea product. Major markets are professional lawn care and professional turf. Formolene Plus ® is manufactured by Arcadian Corporation at Clinton, Iowa and also is toll manufactured by Borden Chemical at about 8 other U.S. locations. |
| CoRoN Corporation | | | | |
| CoRoN ® | 28-0-0 | 0% | 0% | A patented amine-modified polymethylene urea solution fertilizer that was introduced in 1987. Principal markets are professional lawn care and professional turf. Product is also used for foliar and soil applications for vegetables. |
| C. P. Chemical Company, Inc. Growth Products Ltd. Division | | | | |
| Nitro-26 CFN ® | 26-0-0 | 11.5% | 3% | A methylene diurea product for turf and horticultural applications. Principal market is professional lawn care. |
| Georgia-Pacific Corporation | | | | |
| GP-4340 | 30-0-0 | 0% | 0% | Methylol urea products for professional lawn care. Sold direct to major agronomically based lawn care companies. Sales and services to smaller |
| GP-4341 | 30-0-2 | 0% | 0% | |

-continued

Urea-Formaldehyde Fertilizer Products
Marketed in the United States - 1990

| Product, Supplier, and Trade Name | Analysis (N-P-K) | Water-Insoluble Nitrogen (WIN) Percent of Total N | Percent of Product Weight | General Use/Remarks |
|---|---|---|---|---|
| | | | | lawn care companies, golf courses, and other professional turf customers are handled by Nice'N Green Plant Foods, Romeoville, Illinois. Nice'N Green markets GP4340 as NG 1515. |
| Morral Chemical Company | | | | |
| NBN | 30-0-0 | 0% | 0% | Markets are golf courses and professional lawn care, mainly in Ohio. |
| UF-Ammonia Solutions | | | | |
| Arcadian Corporation Triazone Division | | | | |
| N-Sure ® | 28-0-0 | 0% | 0% | A urea-triazone solution fertilizer that was introduced in 1985. Nationwide marketing began in 1986. Principal market is professional lawn care. The product is also sold to O. M. Scott and other companies for use in proprietary liquid fertilizer products for the consumer and professional turf markets. |
| Trisert ® | 13-3-4 (see remarks) | 0% | 0% | Trisert ® 13-3-4 is the basic product in a lines of solution fertilizers based on urea-triazone, which are designed for foliar application to high-value specialty agricultural crops. |
| UF Suspensions | | | | |
| Borden, Inc. Gorden Chemical Division | | | | |
| FER 700 | 18-0-0 | na | na | Product is manufactured for Chem-Lawn Corporation |
| W. A. Cleary Corporation | | | | |
| FLUF ® 18-0-0 | 18-0-0 | 25% | 4.5% | A flowable UF formulation. Principal markets are professional lawn care and golf courses. Product is manufactured for W. A. Cleary by Borden Chemical and Morral Chemical Company. |
| FLUF ® 16-2-4 | 16-2-4 | na | na | Mixed-grade UF suspension fertilizers for golf courses. |
| FLUF ® 10-10-10 Georgia-Pacific Corporation | 10-1-10 | 25% | 2.5% | |
| RESI-GROW ® (GP-4318) | 18-0-0 | 15–25% | 5% | Sold direct to major agronomically based lawn care companies. Sales and services to smaller lawn care companies, golf courses, and other professional turf customers are handled by Nice'N Green Plant Foods. Nice'N Green markets this product as NG 612. |
| UF-Ammonia Solutions | | | | |
| Arcadian Corporation Triazone Division | | | | |
| N-sure ® | 28-0-0 | 0% | 0% | A urea-triazone fertilizer that was introduced in 1985. Nationwide marketing began in 1986. Principal market is professional lawn care. The products is also sold to O. M. Scott and other companies for use in proprietary liquid fertilizer products for the consumer and professional turf markets. |
| Trisert ® | 13-3-4 (see remarks) | 0% | 0% | Trisert ® 13-3-4 is the basic product in a line of solution fertilizers based on urea-triazone, which are designed for foliar application to high-value specialty agricultural crops. |
| UF Suspensions | | | | |
| Borden, Inc. Borden Chemical Division | | | | |
| FER 700 | 18-0-0 | na | na | Product is manufactured for Chem-Lawn Corporation. |
| W. A. Cleary Corporation | | | | |
| FLUF ® 18-0-0 | 18-0-0 | na | 4.5% | A flowable UF formulation. Principal markets are professional lawn care and golf courses. Product |

-continued

Urea-Formaldehyde Fertilizer Products
Marketed in the United States - 1990

| Product, Supplier, and Trade Name | Analysis (N-P-K) | Water-Insoluble Nitrogen (WIN) | | General Use/Remarks |
|---|---|---|---|---|
| | | Percent of Total N | Percent of Product Weight | |
| FLUF® 16-2-4 | 16-2-5 | 25% | na | is manufactured for W. A. Cleary by Borden Chemical and Morral Chemical Company. Mixed-grade UF suspension fertilizers for golf courses. |
| FLUF® 10-10-10 Morral Chemical Company | 10-10-10 | na | 7.5% | |
| UWIN | 18-0-0 | na | na | Markets are golf courses and professional lawn care, mainly in Ohio. |

*NOR-AM Chemical Company is a subsidiary of Schering Berlin, Inc.

The UF resins preferably contain 10%–40% nitrogen, 0%–34phosphorous and 0%–12% potassium, where any UF fertilizer which contains insoluble nitrogen in the range of 5%–40% is most preferred. Examples of preferred fertilizers are UF-1 (12-12-12), TRISERT (13-3-4) a fertilizer solution containing triazone available from the Triazone Corporation. FLUF® (16-2-4), FLUF® (10-0-10) plus 10 mM $K_2HPO_4$ and HAIFATERT (29-0-0) plus HAIFATERT (0-34-9).

It has also been discovered that certain cultures produced factor(s)—probably an enzyme or enzymes—which rapidly converts insoluble high molecular weight UF resins into low molecular weight utilizable nitrogen and phosphorous compounds. These factors can act in the absence of the microbial cells after the cells are disrupted. It is, therefore, a further modification of the invention, that the cell-free supernatant, which is obtained after the cells are harvested from the fermented mixture and are then disrupted, and which contain the UF degrading factor, can be used to provide utilizable nitrogen and phosphorous compounds. It is also part of the present invention, that the cell-free supernatant containing the UF degrading factors in crude or purified form, can be produced in suitable fermentation equipment.

The cell-free supernatant from the bacteria have a urea-formaldehyde utilization activity (UFU) of 200 units, most preferably at least about 400 units, where the UFU activity is defined as the catalytic breakdown of high molecular weight insoluble UF resins into low molecular weight units which are water soluble and dialyzable.

While the invention will now be described in connection with certain preferred embodiments in the following examples, it will be understood that it is not intended to limit the invention to these particular embodiments. On the contrary, it is intended to cover all alternatives modifications and equivalents, as may be included within the scope of the invention as defined by the appended claims. Thus, the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

Isolation of Petroleum-utilizing Bacteria from Sea Water using UF-1 as the Source of Nitrogen and Phosporous A mixed bacterial culture was obtained by enrichment culture procedure using crude oil as the carbon and energy source, UF-1 resin as the nitrogen and phosphorous source and sea water as the source of other minerals. The enrichments were carried out in CO-UF1 medium which consists of 0.5% crude oil (v/v), 0.1% UF-1 and sterile filtered sea water. The enrichment was carried out by inoculating 10 ml of the CO-UF1 medium in a 125 ml flask with tar (collected from Tel Baruch Beach, Tel Aviv) and incubating the mixture at 25° C. with reciprocal shaking (100 strokes per minute). After 3 days, 1 ml of the culture was transferred to 19 ml of sterile CO-UF1 medium and incubation was carried out as above. The procedure was repeated two additional times, after the third transfer a turbid culture was obtained after inoculation and overnight growth. This culture is referred to as "the mixed culture". Microscopic examination indicated that the mixed culture consisted of several different types of motile and non-motile bacteria. The mixed culture was maintained by weekly transfers to fresh sterile CO-UF1 medium.

Three pure cultures, able to grow on CO-UF1 medium, were obtained from the mixed culture by spreading a dilution of the mixed culture onto marine agar (8.7 g marine broth MA.2216, 1.6 g agar, both from Difco Laboratories, Detroit, Mich., and 10 g NaCl per liter deionized water).

After incubation for 3 days at 25° C., three different colony types were isolated by restreaking on marine agar. These strains are referred to as ER-RL3, ER-RL4 and ER-RT. Each of the pure strains was able to grow on and emulsify crude oil in CO-UF1 medium.

EXAMPLE 2

Isolation of Petroleum-utilizing Bacteria from Tap Water using UF-1 as the Source of Nitrogen and Phosphorous A mixed bacterial culture was obtained by enrichment culture procedure using crude oil as the carbon and energy source, and UF-1 as the nitrogen and phosphorous source. The enrichment was performed in a medium which consisted of tap water containing 0.5% crude oil (v/v), 0.1% UF-1 and 0.04% $MgSO_4$ (CO-UF1-2 medium). The source of bacteria was oil-contaminated soil. The soil used was obtained from different locations in the U.S.A. and in Israel. The enrichment was carried out by inoculating 10 ml of the CO-F1-2 medium in a 125 ml flask and incubating the mixture at 25° C. with reciprocal shaking (100 strokes per min). After 3 days, 1 ml of the culture was transferred to 19 ml of sterile medium and incubation was carried out as above. The procedure was repeated two additional times, after the third transfer, turbid cultures were obtained after inoculation and overnight growth. These cultures were referred to as "the mixed cultures". Microscopic examination indicated that each mixed culture consisted of several different types of motile and non-motile bacteria. The mixed cultures were maintained by weekly transfers to fresh sterile medium.

Several pure cultures able to grow on CO-UF1-2 medium were obtained from the mixed cultures by spreading a dilution of the mixed culture onto nutrient agar (from Difco Laboratories, Detroit, Mich.). Two different colony types were isolated by restreaking on agar. These strains are referred to as ER-RL-D and ER-RL-X, the latter isolated from U.S. soil. Each of the pure strains was able to grow on and emulsify crude oil in CO-UF1-2 medium.

EXAMPLE 3

Growth of the Mixed Culture from Sea Water

Figure 1:
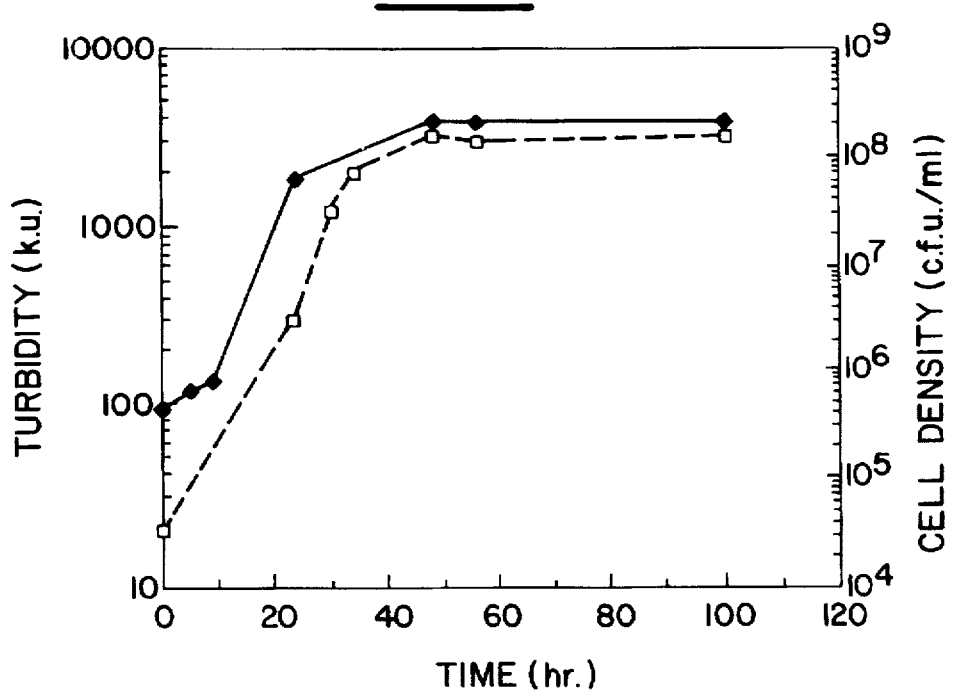
FIG. 1. Kinetics of Growth and Emulsification Ability of the Mixed Culture on Crude Oil/UF-1

The kinetics of growth of tie mixed culture on crude oil is shown in FIG. 1. The mixed culture had a doubling time of approximately 2 hours, reaching stationary phase after 40 hours at $2 \times 10^8$ cells/ml. Growth preceded emulsification by approximately 5 hours. The pH of the growth medium decreased from an initial value of 7.8 to a minimum of 6.8 at 24 hours, and then increased to a final value of 7–7.2. The turbidity of the culture rose sharply up to 3200 k.u., mostly because of emulsification of the oil.

EXAMPLE 4

Dependence of Growth of Mixed Culture from Sea Water on UF-1 and Crude Oil

The results summarized in Table 1 indicate that growth of the mixed culture is dependent on crude oil as carbon source and on UF-1 as nitrogen source. Similar results were obtained with each of the three pure Cultures: growth and emulsification depended upon the presence of both crude oil and UF-1.

EXAMPLE 5

Dependence of Growth of Mixed Cultures of UF-1 and Crude Oil.

The results summarized in Table 2 indicate that growth of ER-RL-D is dependent on crude oil as the carbon source and on UF-1 as the nitrogen source. Similar results were obtained with ER-RL-X: Growth and emulsification depended upon the presence of both crude oil and UF-1.

TABLE 1

| | Utilization of crude oil and UF-1 by mixed culture* from sea water | | |
|---|---|---|---|
| UF-1 (%) | Crude oil (%) | Turbidity (k.u.) | Cell density (CFU/ml) |
| 0.1 | 0 | 24 | $1.0 \times 10^6$ |
| 0.1 | 0.05 | 75 | $1.3 \times 10^7$ |
| 0.1 | 0.02 | 97 | $5.5 \times 10^7$ |
| 0.1 | 0.05 | 256 | $6.0 \times 10^7$ |
| 0.1 | 0.1 | 435 | $7.8 \times 10^7$ |
| 0.1 | 0.5 | 1320 | $1.6 \times 18^8$ |
| 0.1 | 1.0 | 1400 | $2.0 \times 10^8$ |
| 0 | 0.5 | 22 | $3.0 \times 10^6$ |
| 0.05 | 0.5 | 800 | $1.4 \times 10^8$ |
| 0.2 | 0.5 | 1200 | $1.5 \times 10^8$ |
| 0.5 | 0.5 | 1250 | $1.5 \times 10^8$ |
| 1.0 | 0.5 | 2000 | $4.0 \times 10^8$ |
| 1.6 | 0.5 | 2650 | $4.0 \times 10^8$ |

*= The experiment was carried out as described in FIG. 1, except that the concentrations of UF-1 and crude oil were varied as indicated and the sample time was 48 hours.

TABLE 2

| Utilization of crude oil and UF-1 by ER-RL-D. | | | |
|---|---|---|---|
| UF-1 (%) | Crude Oil (%) | Turbidity (k.u.) | Cell density (CFU/ml) |
| 0.1 | 0 | 24 | $1.0 \times 10^6$ |
| 0 | 0.5 | 22 | $3.0 \times 10^6$ |
| 0.1 | 0.5 | 1300 | $2.0 \times 18^8$ |

EXAMPLE 6

Characterization of Marine Strains with UFU Activity

From the mixed culture in sea water, three pure strains that could grow on crude oil and UF-1 (see FIGS. 2, 3 and 4) were isolated and characterized. The properties of these strains are described in Table 3. FIGS. 2, 3 and 4 show the kinetics of growth and emulsification of the three strains ER-RL3, ER-RL4 and ER-RT, respectively. All tie strains have the ability to grow and emulsify oil, using UF-1 resin as a nitrogen and phosphorus source. The strain showed similar doubling times of approximately 3 hr. Strain ER-RT reached the highest growth density ($2 \times 10^8$ c.f.u./ml) although its emulsification (100 k.u.) ability was almost the same as the two other strains. The pH in the growth media in all the strains decreased from an initial value of 7.8 to about 7 at the end of the growth experiment after 72 hours. Here, as in the case of the mixed culture, the turbidity of the cultures came mostly from tile emulsified oil.

EXAMPLE 7

Characterization of Fresh Water Strains with UFU Activity

From the mixed culture obtained on (CO-UF-1-2 medium, two pure strains that could grow on crude oil and UF-1 were isolated and characterized. The properties of these gram-negative strains are described in Table 4. Both strains have the ability to grow and emulsify oil, using UF-1 resin as a nitrogen and phosphorus source.

TABLE 3

| Characterization of strains from CO-UF-1 medium | | | |
|---|---|---|---|
| | Strain | | |
| Property | ER-RL3 | ER-RL4 | ER-RT |
| Colony of marine agar | | | |
| diameter | 2 mm | <1 mm | 1–2 mm |
| color | white | white | yellowish |
| Bacterial shape | rod | rod | rod |
| Dimensions of cells (μm) | | | |
| from marine agar (16 h) | 0.3/1.5 | 0.6/1.2 | 0.6/1.0 |
| from broth on oil (72 h) | 0.5/1.6 | 0.5/2.2 | 0.44/1.1 |
| Motility | + | + | + |
| Flagellar arrangement | | | |
| from marine agar (16 h) | peritrichal | polar | none |
| from broth on oil (72 h) | none | polar | none |
| Growth temperature, °C. | | | |
| 4° C. (100 h) | − | − | − |
| 20° C.–25° C. (24 h) | + | + | + |

TABLE 3-continued

Characterization of strains from CO-UF-1 medium

| Property | Strain ER-RL3 | ER-RL4 | ER-RT |
|---|---|---|---|
| 37° C. (24 h) | + | + | + |
| 41° C. (100 h) | − | − | − |
| NaCl (6%) tolerance | + | + | + |
| NaCl requirements for growth | − | + | + |
| Lipase | + | + | + |
| Oxidase | + | + | + |
| Catalase | + | + | + |
| Starch hydrolysis | − | + | + |
| Urease | − | − | − |
| Plasmids | − | 2 > 60 kb | 2 > 60 kb 1  3 kb |
| Antibiotic sensitivity | | | |
| ampicillin | S | S | S |
| tetracycline | R | R | R |
| penicillin G | S | S | R |
| erythromycin | S | S | S |
| nalidixic acid | S | R | R |
| Utilization of carbon source | | | |
| decane | + | + | + |
| n-hexane (vapour) | + | + | − |
| toluene | − | − | − |
| xylene | + | − | − |
| naphthalene | − | − | − |
| hexadecane | + | + | + |
| tetradecane | + | ++ | − |
| glucose | + | − | + |
| acetate | + | + | + |
| lactate | + | + | + |
| succinate | + | + | + |
| citrate | − | + | + |
| ethanol | − | + | + |
| maltose | + | + | + |
| lactose | − | − | − |
| starch | + | + | − |
| crude oil | + | + | + |
| solar | + | + | + |
| iso-octane | + | + | − |

Classification:
ER-RL4 - *Pseudomonadaceae* genus Pseudomonas.
ER-RL3 - *Pseudomonas alcaligenes* or Alcaligenes (has several degenerate peritrichous flagella)
ER-RT - Pseudomonadaceae genus Gluconobacter

TABLE 4

Characterization of strains from CO-UF-1-2 medium

| Property | Strain ER-RL-D | ER-RL-X |
|---|---|---|
| Colony on salt-ethanol agar plates | | |
| diameter | 2 mm | 2 mm |
| colour | white | white |
| Bacterial shape | short rod | short rod |
| Motility | − | − |
| Growth temperature, °C. | | |
| 4° (100 h) | − | − |
| 20–25° (24 h) | + | + |
| 37° (24 h) | + | + |
| 41° (100 h) | − | − |
| Cytochrome oxidase | − | − |
| Urease | − | +/− |
| Reduction of nitrates | − | − |
| Reduction of nitrates | − | − |
| Indole production | − | − |

TABLE 4-continued

Characterization of strains from CO-UF-1-2 medium

| Property | Strain ER-RL-D | ER-RL-X |
|---|---|---|
| Glucose acidification | − | − |
| Arginine dehydrogenase | − | − |
| Gelatine hydrolysis | − | + |
| Assimilation of C-sources | | |
| glucose | − | + |
| arabinose | − | + |
| mannose | − | − |
| mannitol | − | − |
| N-acetyl-glucosamine | − | − |
| maltose | − | − |
| gluconate | − | − |
| caprate | + | + |
| adipate | − | − |
| malate | + | + |
| citrate | + | + |
| Antibiotic sensitivity | | |
| penicillin G | +/− | +/− |
| ampicillin | +/− | +/− |
| tetracycline | S | S |
| palidixic acid | S | S |
| chloramphenicol | S | S |
| kanamycin | S | S |

Classification: *Acinetobacter calcoaceticus*

The DNA of both strains was able to transform competent auxotrophic cells of *Acinetobacter calcoaceticus* BD413 to prototrophy (Juni and Hanick, Journal of Bacteriology 98:281–288, 1969).

TABLE 5

Growth Of Pure Cultures from Sea Water On Commercial UF Fertilizers[a]

| | Strains | | | | | |
|---|---|---|---|---|---|---|
| Fertilizer (N-P-K) | ER-RL3 CFU/ml | E[b] | ER-RL4 CFU/ml | E[b] | ER-RT CFU/ml | E[b] |
| 1. UF-1 (12-12-12) | 4 × 10$^7$ | ++ | 3 × 10$^8$ | ++ | 7 × 10$^7$ | ++ |
| 2. TRISERT (13-3-4) | 2 × 10$^8$ | + | 3 × 10$^8$ | + | 4 × 10$^6$ | − |
| 3. Fluf (16-2-4) | 4 × 10$^7$ | ++ | 4 × 10$^8$ | + | 2 × 10$^5$ | − |
| 4. Fluf (10-0-10) + 10 mM K$^2$HPO$_4$ | 4 × 10$^7$ | + | <10$^5$ | − | 4 × 10$^6$ | − |
| 5. Haifatest (29-0-0) plus Haifatest (0-34-9) | 2 × 10$^8$ | + | 5 × 10$^8$ | + | 5 × 10$^7$ | − |

[a] = Inocula were grown on the same media, but with different fertilizers. The fertilizer was used at a concentration of 0.1 mg/ml nitrogen and a minimum of 0.01 mg/ml of phosphorus. Colony forming units per ml (CFU/ml) were determined every 24 hours.
[b] = E = Emulsification of oil.

EXAMPLE 8

Range of Polymers Utilized by Strains ER-RL3, ER-RL4 and ER-RT as N and P Sources Different commercial urea formaldehyde slow release fertilizers could support the growth and crude oil utilization ability of the strains ER-RL3, ER-RL4 and ER-RT (Table 5). Strain ER-RL3 grew on all the UF- fertilizers tested. The best growth was obtained on Triazone and a mixture of high nitrogen UF fertilizer (20-0-0) with a high phosphorous slow release fertilizer (0-34-0). Emulsification of the crude oil was obtained in each case, the strongest obtained with UF-1 resin and Fluf (16-2-4) resin. Strain ER-RL4 grew well on crude oil on all UF fertilizers except the one containing no phosphorous (10-0-10), which was supplemented with inorganic phosphate. Strain ER-RT showed a preference for UF-1.

EXAMPLE 9

Range of Polymers Utilized by the Microorganisms as Nitrogen and Phosphorous Sources Different commercial urea-formnaldehyde and triazone slow release fertilizers could support the growth and crude-oil utilization ability of strains ER-RL3, ER-RL-4, ER-RT, ER-RL-X and ER-RL-D.

The strains utilize formaldehyde-urea polymers of both low molecular weight (soluble in water) and high molecular weight (insoluble in water), as demonstrated in Table 6. The separation between low molecular weight (soluble) polymers and high molecular weight (insoluble) polymers was performed by dialysis, the pore size allowing the passage of molecules smaller than 12,000 molecular weight. In addition, both ER-RL-D and ER-RL-X used triazone as a source of nitrogen and phosphorous.

TABLE 6

Growth of Individual Strains on UF-1 of Low and High Molecular Weight[a]

| | CFU/ml after 42 hours of growth | | |
|---|---|---|---|
| Strain | High M.W. resin | Low M.W. resin | TRISERT |
| ER-RL3 | $1.5 \times 10^9$ | $2.0 \times 10^9$ | |
| ER-RL4 | $6.0 \times 10^9$ | $2.5 \times 10^9$ | |
| ER-RT | $8.2 \times 10^9$ | $2.0 \times 10^9$ | |
| ER-RL-D | $1.0 \times 10^8$ | $2.5 \times 10^8$ | $1 \times 10^7$ |
| ER-RL-X | $5.0 \times 10^8$ | $2.5 \times 10^8$ | $6 \times 10^7$ |

[a]= Cells were grown in the standard medium previously described (CO-UF1 for the sea water medium and CO-UF1-2 for the tap water medium), containing 0.1% crude oil and 0.1% fertilizer. The initial cell concentration was $1 \times 10^6$. To obtain high and low molecular weight UF-1, the UF-1 was suspended in water (sea water for ER-RL-3, ER-RL-4, and ER, RE and tap water for ER-RL-D and ER-RL-X), and dialyzed against the water for 4 days. The UF-1 remaining in the dialysis bag is the high molecular weight fraction and the material passing the membrane is the low molecular weight fraction.

EXAMPLE 10

A Simulated Open System Experiment Demonstrating Adherence of UF-1 to the Oil Using Microorganisms Growth in CO-UF-1 Medium One of the major problems with supplementing a contaminated oil spill in the sea with water-soluble nitrogen and phosphorous compounds is, that they will not be concentrated near the oil, where the growth must occur. Rather the compounds will spread and dilute in the open system. It was therefore interesting to test whether or not this problem could be overcome by use of the fertilizer UF-1. The procedure that was used compared growth and emulsification (turbidity) after the fertilizer or soluble nutrients and oil were mixed and the aqueous phase was removed and replaced with fresh sea water. The data (Table 7) clearly show, that UF-1 resin can support growth on crude oil even after the aqueous phase had been removed and replaced twice with fresh sea water containing no additions. None of the cultures that received ammonium sulfate and phosphate salts in place of UF-1 resin and treated in a similar manner grew significantly. This demonstrates that the soluble nutrients were efficiently removed by the wash out process. The pure strains ER-RL3, ER-RL4 and ER-RT and the mixed culture grew after the dilution procedure, reaching more than $10^7$ cell/ml and high values of turbidity. The mixed culture showed the highest ability to grow, reaching $1 \times 10^8$ cells/ml and 900 k.u. Strain ER-RL3 was almost as effective as the mixed culture in growth yield and emulsificatioon of the crude oil.

TABLE 7

Growth of ER-RL4, ER-RL3 and ER-RT on crude oil and UF-1 Following Removal of Water Soluble Nutrients[a]

| | Cell Density (CFU/ml) time 0 | | time 120 h | | Turbidity (k.u.) time 120 h | |
|---|---|---|---|---|---|---|
| Strain | UF-1 | AS | UF-1 | AS | UF-1 | AS |
| ER-RL4 | $5.0 \times 10^5$ | $6.0 \times 10^5$ | $9.0 \times 10^7$ | $4.0 \times 10^5$ | 550 | 22 |
| ER-RL3 | $8.0 \times 10^5$ | $4.0 \times 10^5$ | $9.0 \times 10^7$ | $2.0 \times 10^6$ | 860 | 25 |
| ER-RT | $3.0 \times 10^5$ | $4.0 \times 10^5$ | $6.0 \times 10^7$ | $2.0 \times 10^6$ | 490 | 20 |
| Mixed culture | $3.0 \times 10^5$ | $5.0 \times 10^5$ | $1.0 \times 10^8$ | $1.0 \times 10^6$ | 900 | 23 |

[a]= UF-1 medium contained 0.2% fertilizer (containing 0.2% nitrogen. AS medium contained 0.1% ammonium sulfate (equivalent to 0.02% nitrogen) and 10 mM phosphate buffer. Both media contained 0.5% crude oil as a carbon source.
[b]= Each 20 ml medium was mixed well and then allowed to stand for 5 minutes, allowing the crude oil and the aqueous phase to separate. The aqueous phase was then removed as completely as possible and replaced with 20 ml fresh sea water. The procedure of removal of the remaining water soluble nutrients was repeated once more. Each flask was then inoculated with 40 µl of a pure or a mixed culture and incubated for 120 hours at 25° C. with shaking. Viable counts were determined after inoculation (time 0) and at 120 hours. Turbidity was measured at 120 hours.

EXAMPLE 11

Secretion of Extracellular Emulsifier

Cells of ER-RL-X were grown in medium containing ammonium sulfate (0.1%) as a nitrogen source and ethanol (0.5%) as a carbon source. When the culture reached the stationary phase of growth (about 109 cells per ml) the cells were removed by centrifugation. The supernatant (7.5 ml) was incubated with crude oil (100 µl) with shaking. The oil was emulsified, indicating the presence of an extracellular emulsifier.

EXPERIMENT 12

UFU (Urea-formaldehyde Utilization) Activity
Partial Characterization and Purification from ER-RL3

Determination of UFU Activity
Principle

UFU activity is defined as the catalytic breakdown of high molecular weight UF (not soluble) into low molecular weight units, which are water soluble and dialyzable.

Bioassay for UFU Activity
Principle

The bioassay is based on determining the breakdown of UF-1 to low molecular weight molecules. The low molecular weight (soluble) fraction is separated by dialysis, as it passes the dialysis bag and is found in the dialyzate. It is then quantitated by growth of ER-RL3 bacteria utilizing it as a sole nitrogen source.

Procedure

Step A—Dialysis (molecular weight exclusion=12,000) of sample to be tested (bacteria, extract etc.) for 24 hours at 40° C. to remove low molecular weight nitrogen and phosphorus. The high molecular weight fraction will be called "Retentive A".

Step B—Dialysis of UF-1, same as in step A. The high molecular weight insoluble fraction will be called "Retentive B".

Step C—Retentive A is incubated together with Retentive B for 24 hours at 30° C. in a dialysis bag (as in Step A), placed in ×200 its volume of sea water. The sea water, which contains—at the end of the incubation—the soluble fraction derived from Retentive B by the cellular fraction of Retentive A, is called "Dialyzate C".

Step D—Dialyzate C is now used as N and P source for an indicator culture. This is performed by adding to this sea water 0.5% sodium acetate as carbon source and $10^5$ bacteria of strain ER-RL3. Growth was followed for 16–24 hours at 30° C.

Definition: One unit of UFU (urea formaldehyde utilization activity supports a×10 multiplication of $10^5$ cells of ER-RL3 under the conditions described above.

The results for ER-RL3 appear in Table 8.

TABLE 8

| | UFU Activity Of Cells | |
|---|---|---|
| Fraction used for bioassay | UFU Activity | |
| (added to dialysis bag in step C) | Growth of ER-RL3 | Units |
| I. Control - no cell added | $1.9 \times 10^7$ | 190 |
| II. Washed whole cells grown of UF-1 | $1.6 \times 10^9$ | 16,000 |

TABLE 8-continued

| | UFU Activity Of Cells | |
|---|---|---|
| Fraction used for bioassay | UFU Activity | |
| (added to dialysis bag in step C) | Growth of ER-RL3 | Units |
| III. Extracellular fluid of II concentrated ×5 by $(NH_4)_2SO_4$ precipitation (70% saturation) | $1.0 \times 10^8$ | 1,000 |

EXAMPLE 13

UFU (Urea-formaldehyde Utilization Activity) Partial Characterization and Purification from ER-RL-D and ER-RL-X.

Following the method described in Example 12 except substituting fresh water in place of sea water, the UFU activity of the strains ER-RL-D and ER-RL-X was determined. The results appear in Table 9.

TABLE 9

| | UFU activity of cells | |
|---|---|---|
| Fraction used for bioassay | UFU activity | |
| (added to dialysis bag in step C) | Growth of RL3 | Units |
| I. Control - no cells added | $8.5 \times 10^5$ | 8.5 |
| II. Washed cells of ER-RL-D grown on UF-1 | $6 \times 10^8$ | 6,000 |
| III. Washed cells of ER-RL-X grown on UF-1 | $2.3 \times 10^9$ | 23,000 |

EXAMPLE 14

Partial Purification of UFU Activity of Sea Water Microorganisms

Procedure

Growth of cells: A preculture was prepared by inoculating one loopful of cells from a single colony on plate into a 100 ml flask containing 20 ml of SWA medium (sea water containing 0.5% sodium acetate and 0.1% UF-1) and incubated at 30° C. for 16–24 hours on a reciprocal shaker (100 strokes per minute). 20 ml of this preculture were inoculated into a 2 liter flask and incubated at 30° C. for 3 days on a reciprocal shaker.

Extraction of protein: Cells were collected by centrifugation for 10 minutes at 10,000×g at 4° C. and the pellet was re-suspended in 3 ml or 0.05M sodium phosphate buffer, pH=7.6. The cell suspension was sonicated for 1 minute in an ice bath, 5 times with 1 minute intervals. The sonicated cell suspension was then centrifuged for 60 minutes at 30,000×g at 4° C.

Ammonium sulfate precipitation): Ammonium sulfate was added to the supernatant with stirring to a final concentration of 70% of saturation. The solution was kept overnight at 4° C. The precipitate was collected by centrifugation and then dissolved in 3 ml of 0.05M sodium phosphate buffer, pH=7.6. The solution was dialyzed twice against 5 liters of water at 4° C.

Ultra-filtration: Protein fractions were ultra-filtered by use of the apparatus and appropriate molecular weight filters of Amicon.

The results of the purification of each strain appear in Table 10. The results of the separation of ammonium sulfate precipitates by molecular weight appear in Table 11.

TABLE 10

Results of Purification

| Cellular Fraction | UFU Activity Growth of ER-RL3 | Protein mg/ml | Units |
|---|---|---|---|
| ER-RL3 | | | |
| Cell extract | $4.2 \times 10^8$ | 1 | 4,200 |
| Supernatant activity after $(NH_4)_2SO_4$ precipitation | $3 \times 10^6$ | 0.125 | 30 |
| ER-RL4 | | | |
| Cell extract | $8 \times 10^7$ | 0.65 | 870 |
| Supernatant activity after $(NH_4)_2SO_4$ precipitation | $1.5 \times 10^6$ | 0.06 | 15 |
| ER-RT | | | |
| Cell extract | $3.0 \times 10^8$ | 0.9 | 3,000 |
| Supernatant activity after $(NH_4)_2SO_4$ precipitation | $2.5 \times 10^6$ | 0.065 | 25 |
| No protein added | $2 \times 10^6$ | 0 | 20 |

TABLE 11

Separation of Ammonium Sulfate Precipitates By Molecular Weight

| Molecular Weight | Units of Activity |
|---|---|
| ER-RL3 total protein | 1,296 |
| >300,000 | 34 |
| <300,000 | 900 |
| 100,000> <300,000 | 20 |
| >50,000 | 799 |
| <50,000 | 41 |
| Control | 28 |

EXAMPLE 15

Enhance Biodegradation of Hydrocarbon Contaminated Beach Sand Using Microorganisms Isolated from Sea Water

Experimental Procedures

A. Site Selection and Characteristics

Two plots of 50 $m^2$ were selected, one for the experiment and the second for the control. They were located approximately 30 m from the water line, about 3 km north of Zvulun Beach (Kiryat Yam). The plots were chosen because they were representative of the oil polluted sands. The oil polluted about 5 cm in depth. The initial concentration of oil (pentane-extractable) in the upper 10 cm was 0.23% and 0.38% in the control and in the experimental plots, respectively. The moisture content of the sand was 4%–5%. The unpacked density of the sand was 1.27 g/cm³. The maximum temperature of the sand was 36° C. at noon.

B. Initial Treatment

The experimental plot was inoculated with 20 of a mixed bacterial culture containing strains ER-RL3, ER-RL4 and ER-RT. UF-1 (38 kg in the form of a fine powder) was added as the source of nitrogen and phosphorous. The plot was then watered with sea water from the adjacent sea (water temperature was 27° C.). The plot was then tilled by hand with the help of a simple rake to the depth of about 5 cm.

The control plot was left undisturbed.

C. Daily Treatment

After the first day, the experimental plot was watered daily between 15:00–16:00 with approximately 1.5 $m^2$ sea water with the help of a SUB 3000 GR submergible pump attached to a hose. After watering, the plot was raked to a depth of about 5 cm.

D. Sampling Procedure

Ten random core samples (5 cm diameter×10 cm depth) were taken prior to the daily watering from both the experimental and control plots. The samples were mixed thoroughly in the field, placed in a plastic bag and brought to the laboratory. The sand was either extracted the same day or stored overnight at 4° C.

E. Determination of Residual Petroleum in the Sand

For each time point, triplicate 5 g samples were extracted and the results presented are the average of the three values. Each 50 g sample was placed in a 500 ml bottle that contained 50 ml n-pentane. After shaking vigorously for 5 minutes, 25 ml of the pentane extract were transferred to a 100 ml flask containing anhydrous $CaCl_2$. After standing for 5 minutes with occasional stirring, the dried pentane extract was filtered through Whatmann 2 V paper and then evaporated in vacuo (water aspirator) at 30° C. The residual hydrocarbon was dissolved in 3 ml n-pentane and placed in small glass vials in a chemical hood. The weight of the pentane-extractable hydrocarbon was determined by weighing to constant weight at room temperature on an analytical balance. A control of n-pentane taken through the same procedure contained 0.54 mg residues per 100 ml pentane. Thus, the contribution of the non-volatiles in the pentane to the values reported was 0.006 mg/g sand, which is negligible. The values reported were, however, corrected for the moisture content of the specific sand sample.

RESULTS

The experimental data are presented in Tables 12 and 13. On day zero (Sep. 1, 1991), the core samples were taken prior to any treatment. At the beginning of the experiment, the experimental plot contained significantly more hydrocarbon (3.80 mg/g sand) than the control plot (2.3 mg/g sand). There was only a small decrease in the first day. However, by the fourth day 30% of the hydrocarbon had been degraded. The bio—degradation continued, reaching 50% on day 9 and 84.5% on day 25, when the experiment was concluded.

The control plot showed a 18% degradation by day to day were not due to the pentane extraction procedure, because the average standard deviations were very low (0.03 mg/g sand, corresponding to less than ±2%). Therefore we assume that the core sampling was probably the source of the day to day variation.

SUMMARY

Enhanced biodegradation (bacteria+nutrient UF-1) of the contaminated sands was successful, reaching 84.5% degradation after 25 days, compared to an untreated control, which leveled off at less than 20%.

TABLE 12

Enhanced biodegradation of hydrocarbon-contaminated beach sand.

| Day | Pentane-extractables[a] mg/gram sand | % degradation |
| --- | --- | --- |
| 0 | 3.80 | 0 |
| 1 | 3.70 | 2.6 |
| 4 | 2.76 | 30 |
| 9 | 1.89 | 50 |
| 14 | 0.88 | 77 |
| 21 | 1.40 | 63 |
| 25 | 0.59 | 84.5 |

[a]- Each value is the average of three determinations. The average standard deviation was 0.1 mg/gram sand for the experimental value and 0.15 mg/gram for the control value.

TABLE 13

Natural biodegradation of hydrocarbon-contaminated beach sand

| Day | Pentane-extractables[a] mg/gram sand | % degradation |
| --- | --- | --- |
| 0 | 2.30 | 0 |
| 4 | 2.53 | 0 |
| 9 | 1.88 | 18 |
| 14 | 1.70 | 26 |
| 21 | 1.94 | 15.6 |
| 25 | 1.95 | 15.6 |

[a]—Each value is the average of three determinations. The average standard deviation was 0.1 mg/gram sand for the experimental value and 0.15 mg/gram for the control value.

We claim:

1. A composition prepared for the application to a soil or water composition having the capability of bioremediation of the hydrocarbons content of liquid and heavy tar hydrocarbon-polluted soil or water compositions, consisting essentially of (a) at least one bacterium preselected to be functionally capable of metabolizing said hydrocarbons, and (b) triazone, in a form which permits the microorganism to maintain growth and replication during metabolism of said hydrocarbons.

2. A composition prepared for the application to a soil or water composition having the capability of bioremediation of the hydrocarbons content of liquid and heavy tar hydrocarbon-polluted soil or water compositions, consisting essentially of (a) at least one Pseudomonas bacterium preselected to be functionally capable of metabolizing said hydrocarbons, and (b) a water insoluble, at ambient temperatures, source of nutrient nitrogen in a form which permits the microorganism to maintain growth and replication during metabolism of said hydrocarbons.

3. A composition prepared for the application to a soil or water composition having the capability of bioremediation of the hydrocarbons content of liquid and heavy tar hydrocarbon-polluted soil or water compositions, consisting essentially of (a) at least one Acinetobacter bacterium preselected to be functionally capable of metabolizing said hydrocarbons, and (b) a water insoluble, at ambient temperatures, source of nutrient nitrogen in a form which permits the microorganism to maintain growth and replication during metabolism of said hydrocarbons.

* * * * *